(12) United States Patent
Sugiyama et al.

(10) Patent No.: US 10,143,601 B2
(45) Date of Patent: Dec. 4, 2018

(54) DISPOSABLE DIAPER

(71) Applicants: OJI NEPIA CO., LTD., Tokyo (JP);
OJI HOLDINGS CORPORATION, Tokyo (JP)

(72) Inventors: Katsuhiko Sugiyama, Tokyo (JP);
Izumi Tashiro, Tokyo (JP); Ikuko Furukawa, Tokyo (JP)

(73) Assignees: OJI NEPIA CO., LTD., Tokyo (JP);
OJI HOLDINGS CORPORATION, Tokyo (JP)

( * ) Notice: Subject to any disclaimer, the term of this patent is extended or adjusted under 35 U.S.C. 154(b) by 641 days.

(21) Appl. No.: 14/438,880

(22) PCT Filed: Jul. 31, 2013

(86) PCT No.: PCT/JP2013/070746
§ 371 (c)(1),
(2) Date: Apr. 28, 2015

(87) PCT Pub. No.: WO2014/069062
PCT Pub. Date: May 8, 2014

(65) Prior Publication Data
US 2015/0290048 A1    Oct. 15, 2015

(30) Foreign Application Priority Data
Oct. 29, 2012   (JP) .................................. 2012-237454

(51) Int. Cl.
*A61F 13/49*   (2006.01)
*A61F 13/56*   (2006.01)

(52) U.S. Cl.
CPC .. *A61F 13/49017* (2013.01); *A61F 13/49011* (2013.01); *A61F 13/5622* (2013.01);
(Continued)

(58) Field of Classification Search
CPC ............ A61F 13/4758; A61F 13/49009; A61F 13/49011; A61F 13/49012;
(Continued)

(56) References Cited

U.S. PATENT DOCUMENTS

| 6,676,647 B2 * | 1/2004 | Shimada ........... A61F 13/49011 2/400 |
| 8,109,915 B2 * | 2/2012 | Shimoe ............. A61F 13/49011 604/385.22 |

(Continued)

FOREIGN PATENT DOCUMENTS

| JP | 2006-198207 A | 8/2006 |
| JP | 2008-29749 A | 2/2008 |

(Continued)

OTHER PUBLICATIONS

International Search Report of International application No. PCT/JP2013/070746 completed Aug. 14, 2013 and dated Aug. 27, 2013 (2 pages).

*Primary Examiner* — Lynne Anderson
(74) *Attorney, Agent, or Firm* — Pyprus Pte Ltd (57) ABSTRACT

[Problem] To provide a disposable diaper which is comfortable to wear.
[Solution] This disposable diaper comprises a top sheet (1), a back sheet (2), an absorber (3) and a stretchable sheet (4). The stretchable sheet (4) is composed by having a base material sheet (41) sandwich multiple elastic stretchable members (42) disposed therein in an extended state, said multiple elastic stretchable members (42) being disposed along the width direction of the disposable diaper and spaced apart at intervals in the longitudinal direction. When viewed in the width direction, the stretchable sheet (4) has an overlapping portion (43) which includes a region that overlaps with a part of the absorber (3). In the overlapping portion (43), the multiple elastic stretchable members (42)

(Continued)

are disposed continuously along the width direction. The multiple elastic stretchable members (42) are not joined to the sides of the base material sheet (41) at the central region (43*a*) of the overlapping portion (43), said central region (43) being where part of the absorber (3) is overlapped, and are joined to the sides of the base material sheet (41) at the side regions (43*b*) of the overlapping portion (43) which are positioned to the outside of the central region (43*a*) in the width direction.

4 Claims, 6 Drawing Sheets

(52) U.S. Cl.
 CPC  *A61F 13/5633* (2013.01); *A61F 2013/49022* (2013.01); *A61F 2013/49025* (2013.01)

(58) Field of Classification Search
 CPC .......... A61F 13/49017; A61F 13/49019; A61F 13/49446; A61F 13/49466; A61F 2013/49025; A61F 2013/49028; A61F 2013/49033; A61F 2013/49039; A61F 2013/49041

See application file for complete search history.

(56) References Cited

U.S. PATENT DOCUMENTS

| | | | | |
|---|---|---|---|---|
| 2005/0080394 | A1* | 4/2005 | Otsubo et al. | 13/15 |
| 2006/0282054 | A1* | 12/2006 | Shimoe | A61F 13/49011 604/385.3 |
| 2013/0226121 | A1* | 8/2013 | Kikkawa | A61F 13/539 604/372 |

FOREIGN PATENT DOCUMENTS

| | | |
|---|---|---|
| JP | 2008-188048 A | 8/2008 |
| JP | 2012-91054 A | 5/2012 |
| JP | 2012-200577 A | 10/2012 |

* cited by examiner

DISPOSABLE DIAPER

TECHNICAL FIELD

The present invention relates to a disposable diaper applied to a crotch of a wearer, and for absorbing and holding a liquid such as urine. To be specific, the present invention relates to a disposable diaper in which a stretchable sheet configured such that elastic stretchable members are sandwiched between base material sheets is arranged in a part around a waist at a front body part side or a back body part side, and which enables a part around a trunk to be stretchable.

BACKGROUND ART

Conventionally, as a pant-type or a tape-type disposable diaper, one with a part around the waist of a front body part and a back body part formed stretchable in order to enhance contact properties between the diaper and the body of a wearer is known. To make the part around the trunk of the disposable diaper stretchable, use of woven fabric (stretch fabric), the material of which itself has stretching force, can be considered. However, use of such woven fabric for the disposable diaper is too costly. Therefore, a technology is known, which forms a stretchable sheet by gluing a thread-like or a belt-like elastic stretchable member to a non-stretchable sheet of nonwoven fabric or a plastic film in an extended state to enable the non-stretchable sheet stretchable, and arranges the stretchable sheet around the trunk of the disposable diaper.

As the above-described disposable diaper including the stretchable sheet, the inventions disclosed in Patent Literatures 1 and 2 are known.

In the disposable diaper disclosed in Patent Literature 1, an absorber lies between a top sheet and a back sheet, and the stretchable sheet is arranged in a part around the waist at the back body part side or the front body part side. The stretchable sheet is formed such that a plurality of lines of the elastic stretchable members is glued between base material sheets in an extended state. In the disposable diaper of Patent Literature 1, the elastic stretchable members included in the stretchable sheet are cut into pieces in a region where the stretchable sheet overlaps with the absorber, and are caused to be in a non-stretchable state.

Further, in the disposable diaper disclosed in Patent Literature 2, similarly to the disposable diaper of Patent Literature 1, an elastic strand is joined to the base material sheet in an extended state and a stretchable sheet is formed, and the stretchable sheet is arranged in a part around the waist of the disposable diaper. In the disposable diaper disclosed in Patent Literature 2, the elastic stretchable member included in the stretchable sheet is bonded with pressure by embossing in a region overlapping with the absorber, and the elastic strand does not exist in the region bonded with pressure, or is in a non-stretchable state if existing.

In the disposable diapers described in Patent Literatures 1 and 2, the elastic stretchable member (elastic strand) is in the non-stretchable state in the region where the absorber and the stretchable sheet overlap with each other. With such a configuration, when the stretchable sheet contracts, wrinkles or twists occur in the absorber, and deterioration of feeling of wearing the diapers can be prevented.

CITATION LIST

Patent Literature

Patent Literature 1: JP 2008-29749 A
Patent Literature 2: JP 2006-198207 A

SUMMARY OF INVENTION

Technical Problem

However, there is a problem that, when the elastic stretchable member arranged in the part around the waist is in the non-stretchable state in the region where the elastic stretchable member and the absorber overlap with each other, like the technologies disclosed in the Patent Literatures, a gap is caused between the absorber and the part around the waist of the wearer when the disposable diaper is applied, and contact properties of the diaper are deteriorated. When the contact properties between the diaper and the wearer are deteriorated, a sheet member that configures the diaper may rub the skin of the wearer and damages the skin, and leakage of urine cannot be reliably prevented.

Therefore, to solve the above problems, exertion of stretchability of the stretchable sheet arranged in the part around the waist can be considered even in the region where the stretchable sheet and the absorber overlap with each other. However, if the stretchability of the stretchable sheet is exerted in the region where the stretchable sheet and the absorber overlap with each other, the stretching force of the elastic stretchable member is directly transmitted to the absorber and the wrinkles or twists are caused in the absorber, and the deterioration of feeling of wearing the diaper is incurred.

Therefore, currently, a technology to prevent the occurrence of wrinkles or twists in the absorber while maintaining the contact properties of the absorber and the part around the waist of the wearer is required, even for the disposable diaper with a stretchable sheet arranged in the part around the waist.

Solution to Problem

Therefore, the inventors of the present invention have diligently discussed about solutions to the problems of the above conventional inventions. As a result, a stretchable sheet formed such that a plurality of elastic stretchable members is sandwiched between base material sheets is arranged in a part around a waist of a diaper, and while the elastic stretchable members included in the stretchable sheet are allowed to exist in a region overlapping with an absorber, the elastic stretchable members existing in the overlapping region are not allowed to be joined with the base material sheet. Accordingly, the elastic stretchable members exist in the region where the stretchable sheet and the absorber overlap with each other, and thus the contact properties of the absorber and the part around the waist of the wearer can be maintained. Further, the elastic stretchable members positioned in the region where the stretchable sheet and the absorber overlap with each other is not joined to the base material sheet, and the stretchability is not directly transmitted to the absorber. Therefore, occurrence of wrinkles or twists in the absorber can be prevented. Then, the inventors have arrived at the fact that the problems of the conventional technologies can be solved based on the above-described knowledge, and have completed the present invention.

Specifically describing the present invention, the present invention has the following configuration.

The present invention relates to a disposable diaper.

The disposable diaper of the present invention includes a liquid permeable top sheet 1, a liquid impermeable back sheet 2, an absorber 3 lying between the top sheet 1 and the back sheet 2 in a part including a crotch part, and a stretchable sheet 4 lying between the top sheet 1 and the back sheet 2 in both parts of a front body part and a back body part or one part of the front body part or the back body part.

Here, the stretchable sheet 4 includes a base material sheet 41, and a plurality of elastic stretchable members 42 extending along a width direction of the disposable diaper, and arranged between the base material sheets 41 in an extended state at intervals in a length direction of the disposable diaper.

Further, the stretchable sheet 4 has an overlapping part 43 including a region overlapping with a part of the absorber 3 as viewed in the width direction.

Further, the plurality of elastic stretchable members 42 is continuously arranged along the width direction in the overlapping part 43.

Then, the plurality of elastic stretchable members 42 is not joined between the base material sheets 41 in a central region 43a that overlaps with a part of the absorber 3, of the overlapping part 43, and is joined between the base material sheets 41 in side regions 43b positioned outside the central region 43a of the overlapping part 43 in the width direction.

As described in the configuration, while the plurality of elastic stretchable members 42 included in the stretchable sheet 4 exists in the central region 43a that overlaps with the absorber 3, the plurality of elastic stretchable members 42 is not joined between the base material sheets 41. In this way, the elastic stretchable members 42 are caused to exist in the central region 43a where the stretchable sheet 4 and the absorber 3 overlap with each other, whereby the absorber 3 can be closely attached to the skin of the wearer when the elastic stretchable members 42 contract. Further, the elastic stretchable members 42 exist in the central region 43a where the stretchable sheet 4 and the absorber 3 overlap with each other, so that stretchability of the stretchable sheet 4 is maintained, and thus a part around the waist of the diaper can be well extended, and feeling of wearing the diaper is improved. Meanwhile, the elastic stretchable members 42 are not joined between the base material sheets 41 in the central region 43a where the stretchable sheet 4 and the absorber 3 overlap with each other. Therefore, the absorber 3 cannot be inwardly pulled in the width direction even if the elastic stretchable members 42 contract, and occurrence of wrinkles or twists in the absorber can be prevented. In this way, the present invention realizes maintenance of the contact properties of the absorber, and keeping the shape of the absorber beautiful at the same time.

In the present invention, it is favorable that the stretchable sheet 4 further includes a non-overlapping part 44 not overlapping with the absorber 3 as viewed in the width direction. Then, it is favorable that the plurality of elastic stretchable members 42 is continuously arranged along the width direction and is joined between the base material sheets 41, in the non-overlapping part 44.

As described in the configuration, the stretchable sheet 4 includes the non-overlapping part 44 that is a region not overlapping with the absorber 3 and extending in the width direction, and the plurality of elastic stretchable members 42 are continuously arranged in the non-overlapping part 44, and are joined between the base material sheets 41, whereby the contact properties of not only an end part of the absorber 3, but also its peripheral part are improved. Accordingly, the feeling of wearing the diaper can be more favorable.

It is favorable that the disposable diaper of the present invention further includes at least a pair of right and left fastening parts 5 attached to both of right and left side parts of the front body part or the back body part so as to protrude from both of right and left side edges toward outsides in the width direction. The fastening parts 5 can be fastened to an outer surface of the front body part or the back body part of the diaper. The fastening parts 5 are fastened to the outer surface of the diaper, whereby the disposable diaper can be applied to the part around the waist of the wearer.

In this case, the stretchable sheet 4 is arranged in the part where the fastening parts 5 are provided, of the front body part or the back body part. Then, it is favorable that the plurality of elastic stretchable members 42 included in the stretchable sheet 4 is positioned at inner sides in the width direction of fixed ends where the fastening parts 5 are fixed to the both of right and left side parts.

As described in the configuration, it is favorable that the elastic stretchable members 42 included in the stretchable sheet 4 are positioned at inner sides in the width direction of the fixed ends of the pair of fastening parts 5. A part between the pair of fastening parts 5 corresponds to the part around the waist of the diaper. Therefore, stretchability is provided between the pair of fastening parts 5, whereby the wearer can wear the diaper while pulling the fastening parts 5 when wearing the diaper. Further, the stretchability is provided between the pair of fastening parts 5, whereby the part around the waist of the diaper becomes comfortable. Further, it is favorable that both end parts in the width direction of the plurality of elastic stretchable members 42 included in the stretchable sheet 4 does not overlap with the fixed ends of the fastening parts 5. If the both end parts of the elastic stretchable members 42 overlap with the fastening parts 5, the fastening parts 5 are deformed when the elastic stretchable members 42 contract, and operability of the fastening parts 5 is deteriorated and the disposable diaper can be less easily applied. The both end parts of the elastic stretchable members 42 are caused not to overlap with the fixed ends of the fastening parts 5, whereby such problems can be avoided.

In the present invention, it is favorable that the plurality of elastic stretchable members 42 included in the stretchable sheet 4 is arranged at approximately constant intervals in the length direction. The "approximately constant" referred here includes not only a case where the intervals of the plurality of elastic stretchable members 42 completely accord with each other, but also a case where the plurality of elastic stretchable members 42 is arranged at intervals within a range of error of ±5% or less where an average value of the intervals of the plurality of elastic stretchable members 42 is 100%.

As described in the configuration, the plurality of elastic stretchable members 42 is arranged at approximately constant intervals, whereby gathers (pleats) are uniformly formed in the part around the waist of the diaper, and appearance of the diaper becomes favorable.

In the present invention, it is favorable that the stretchable sheet 4 is arranged with an interval from an end edge of the front body part or the back body part in which the stretchable sheet 4 is arranged in the length direction.

As described in the configuration, the stretchable sheet 4 is arranged with the interval from the end edge of the diaper in the length direction, whereby hardness of the stretchable sheet 4 itself is less likely to be transmitted to the wearer, and the feeling of wearing the diaper is improved.

In the present invention, two-ply or more base material sheets 41 included in the stretchable sheet 4 are layered between the elastic stretchable members 42 and the absorber 3 in the overlapping part 43.

As described above, in the present invention, the elastic stretchable members 42 are not joined between the base material sheet 41 in the central region 43a where the stretchable sheet 4 and the absorber 3 overlap with each other, whereby the absorber 3 cannot be deformed even if the stretchable sheet 41 contracts. Further, in favorable embodiments of the present invention, to further improve the above effect, two-ply or more base material sheets 41 are layered between the elastic stretchable members 42 and the absorber 3 in the overlapping part 43 including the region where the stretchable sheet 4 overlaps with the absorber 3. Accordingly, two-ply or more base material sheets 41 are layered in a place being in contact with the absorber 3. Therefore, contractive force of the elastic stretchable members 42 is less likely to be transmitted to the absorber 3, and the amount of deformation of the absorber 3 can be suppressed.

Advantageous Effects of Invention

In the present invention, while the plurality of elastic stretchable members 42 included in the stretchable sheet 4 is allowed to exist in the central region 43a that overlaps with the absorber 3, the plurality of elastic stretchable members 42 are not allowed to be joined between the base material sheets 41. In this way, the elastic stretchable members 42 are caused to exist in the central region 43a where the stretchable sheet 4 and the absorber 3 overlap with each other, whereby the absorber 3 can be closely attached to the skin of the wearer when the elastic stretchable members 42 contract. Further, the elastic stretchable members 42 exist in the central region 43a where the stretchable sheet 4 and the absorber 3 overlap with each other, whereby the stretchability of the stretchable sheet 4 is maintained. Therefore, the part around the waist of the diaper becomes well extended, and the feeling of wearing the diaper is improved. Meanwhile, the elastic stretchable members 42 are not joined between the base material sheets 41 in the central region 43a where the stretchable sheet 4 and the absorber 3 overlap with each other. Therefore, the absorber 3 cannot be inwardly pulled in the width direction even if the elastic stretchable members 42 contract, and occurrence of wrinkles or twists in the absorber can be prevented. In this way, the present invention realizes maintenance of the contact properties of the absorber, and keeping the shape of the absorber beautiful at the same time.

BRIEF DESCRIPTION OF DRAWINGS

FIGS. 1(a) and 1(b) illustrate an example of a disposable diaper according to an embodiment of the present invention.

FIGS. 4(a) to 4(c) illustrate examples of structures of a stretchable sheet included in a disposable diaper of the present invention.

FIGS. 5(a) and 5(b) illustrate examples of structures of a stretchable sheet included in a disposable diaper of the present invention.

FIGS. 6(a) to 6(d) illustrate examples of structures of a stretchable sheet included in a disposable diaper of the present invention.

DESCRIPTION OF EMBODIMENTS

Hereinafter, embodiments for implementing the present invention will be described with reference to the drawings. The present invention is not limited to the embodiments to be described below, and includes appropriately modified embodiments within a scope apparent for a person skilled in the art from the embodiments below.

Note that, in the specification of the present application, "A to B" means "from A to B, both inclusive".

Further, in the specification of the present application, "length direction" is a length direction of a disposable diaper formed in a longitudinally long shape, and means a direction connecting a front body part and a back body part of the disposable diaper (the up and down direction of FIGS. 1(a) and 1(b)). Further, "width direction" is a width direction of the disposable diaper formed in a longitudinally long shape, and means a direction plenary perpendicular to the length direction (the right and left direction of FIGS. 1(a) and 1(b)). Further, "thickness direction" is a direction into which sheet members that configure the disposable diaper overlap with each other, and means a direction stereoscopically perpendicular to the length direction and the width direction (the right and left direction of FIG. 2).

Further, for easy understanding of a direction in a three-dimensional space, orthogonal coordinates X, Y, Z are illustrated in each of the drawings. In each of the drawings, an X axis represents the width direction, a Y axis represents the length direction, and a Z axis represents a thickness direction.

FIG. 1(a) is a developed diagram illustrating an example of a tape-type disposable diaper 100, and illustrates a state of the disposable diaper 100 as viewed from a side of a surface being in contact with the skin of a wearer (skin contact surface) when the disposable diaper 100 is applied. FIG. 1(b) is a conceptual diagram of an extracted and enlarged stretchable sheet 4 included in the disposable diaper 100.

As illustrated in FIG. 1(a), the tape-type disposable diaper 100 has a longitudinally long shape, and is divided into a front body part 101 that covers a ventral part of the wearer, a back body part 102 that covers a dorsal part of the wearer, and a crotch part 103 that is placed on a crotch of the wearer, in the length direction when the disposable diaper is applied.

The crotch part 103 is a part positioned between the front body part 101 and the back body part 102. The disposable diaper 100 includes an absorber 3 arranged from the front body part 101 to the back body part 102, having the crotch part 3 in the center. The absorber 3 has a function to absorb and hold a liquid such as urine. For example, the absorber 3 is configured such that an absorbent material 31 for absorbing and holding a body fluid or urine of the wearer is covered with core wrap sheets 32 from a skin contact surface side and a skin non-contact surface side. As the absorbent material 31, one obtained such that fluff pulp and super absorbent polymer (SAP) are mixed and formed into a mat shape can be employed, for example. An example of the fluff pulp includes one obtained such that wood pulp or non-wood pulp is fibrillated in a floc manner. An example of the SAP includes sodium polyacrylate. Further, the core wrap sheet 32 is configured from a hydrophilic sheet. As the hydrophilic sheet, a tissue, an absorbent paper, or hydrophilicized nonwoven fabric can be used. It is favorable to form the shape of the absorber 3 such that the absorbent material 31 molded in a sandglass shape, for example, is wrapped between the rectangular core wrap sheets 32 in a planar view as illustrated in FIG. 1(a). Note that, as the shape of the absorbent material 31, a conventional shape such as a rectangular shape, a calabash shape, or a T-shape can be employed, for example.

The absorber 3 is covered with the liquid permeable top sheet 1 from the side of the surface (skin contact surface) being in contact with the skin of the wearer, and is covered with the liquid impermeable back sheet 2 from the side of the surface (skin non-contact surface) not being in contact with the skin of the opposite side. Therefore, the liquid such as urine permeates the top sheet 1 and is absorbed and held in the absorber 3, and is prevented from leaking to an outside by the back sheet 2. As the liquid permeable material that configures the top sheet 1, woven fabric, nonwoven fabric, or a porous film can be employed, for example. In particular, as the liquid permeable material, it is preferable to use hydrophilicized nonwoven fabric made of a thermoplastic resin such as polypropylene, polyethylene, polyester, or nylon. Further, as the liquid impermeable material that configures the back sheet 2, it is favorable to use a liquid impermeable film made of a resin such as polyethylene. In particular, it is as the liquid impermeable material, it is favorable to use a microporous polyethylene film. The microporous polyethylene film is formed with a large number of micro holes of a size of about 0.1 µm. The microporous polyethylene film is liquid impermeable but moisture permeable, and thus can prevent the inside of the diaper from becoming stuffy.

Further, a pair of right and left side sheets 6 may be arranged at both sides of the absorber 3 in the width direction. The side sheets 6 are favorably formed of a material having high breathability while having hydrophobicity. Further, one ends of the side sheets 6 are fixed on the surface of the top sheet 1, and three-dimensional gather stretchable members 61 are fixed to the other ends in an extended state, whereby three-dimensional gathers may be formed. The three-dimensional gathers stand toward a direction being in contact with the skin of the wearer, using contractive force thereof, when the three-dimensional gather stretchable members 61 contracts. The standing three-dimensional gathers function as a leakage preventing wall for preventing leakage of the liquid from right and left sides of the top sheet 1. Further, leg-surrounding gather stretchable members 62 are fixed in an extended state to vicinities of parts of the side sheets 6, in which leg-surrounding openings are formed, whereby leg-surrounding gathers may be formed. By forming of the leg-surrounding gathers, leg-surrounding contact properties of the wearer can be improved when the diaper is applied.

Further, to reinforce the back sheet 2 and to improve the hand feeling, a cover sheet 7 (see FIG. 2) may be pasted to the skin non-contact surface side of the back sheet 2. As a material that forms the cover sheet 7, nonwoven fabric or wet nonwoven fabric made of thermoplastic resin such as polyethylene, polypropylene, or polyester can be used, for example.

Further, as illustrated in FIG. 1(a), the tape-type disposable diaper 100 includes side flaps 101a and 102a in the front body part 101 and the back body part 102, the side flaps 101a and 102a extending toward both of right and left sides in the width direction. A pair of right and left fastening parts 5 is attached to the side flap 102a formed in the back body part 102 so as to protrude from side edges of the right and left side flaps to outsides in the width direction. Each of the pair of fastening parts 5 has a fixed end 51 fixed to overlap with the side flap 102a and a protruding part 52 protruding from the side edge of the side flap 102a. Further, engaging members 53 are provided at the skin contact surface side of the protruding parts 52 of the fastening parts 5. Meanwhile, a front patch 8 for fixing the engaging members 53 of the fastening parts 5 is provided at the skin non-contact surface side of the front body part 101. Therefore, the tape-type disposable diaper 100 can be applied to the wearer by engaging the engaging members 53 of the fastening parts 5 attached to the back body part 102 with front patch 8 provided at the front body part 101 in a state where the back body part 102 is placed over the dorsal part of the wearer, and the front body part 101 is placed over the ventral part of the wearer. The fastening parts 5 and the front patch 8 may be engaged by an adhesive or an adhesive tape, or may configure a mechanically coupled planar fastener. For example, as a fastening mechanism that engages the engaging members 53 of the fastening parts 5 and the front patch 8, it is especially favorable to use a planar fastener that performs fixation by mechanical coupling of a hook material (male member) and a loop material (female member). The planar fastener is configured from a combination of the hook material with a large number of protrusions (a hook shape, a mushroom shape, or the like) on a surface, and the loop material having loop-shaped fiber arranged on a surface, for example. For example, the hook material may be employed as the engaging members 53 of the fastening parts 5, and the loop material may be formed on an outer surface of the front patch 8. In the planar fastener, when the hook material is stuck on the surface of the loop material, the large number of hook materials is engaged with the surface of the loop material. Therefore, the planar fastener can be firmly fixed in a state where the hook material and the loop material are in a re-removable manner, and is favorable in that repetitive use is possible and fixing strength is strong.

Note that the fastening parts 5 can be attached to the side flap 101a of the front body part 101 instead of the side flap 102a of the back body part 102. In this case, the front patch 8 may just be provided at the skin non-contact surface side of the back body part 102. Further, not only one pair but also two or more pairs of the fastening parts 5 can be provided to the right and left side flaps.

In the present invention, a stretchable sheet 4 lies in one part of the front body part 101 or the back body part 101, or both parts of the front body part 101 and the back body part 102 between the top sheet 1 and the back sheet 2. In the embodiment illustrated in FIG. 1(a), the stretchable sheet 4 is arranged in a part of the back body part 102 to which the fastening parts 5 are provided. The stretchable sheet 4 has a structure for allowing a part around the waist of the diaper to exert the stretchability. Hereinafter, a configuration of the stretchable sheet 4 will be specifically described.

Figure 1:
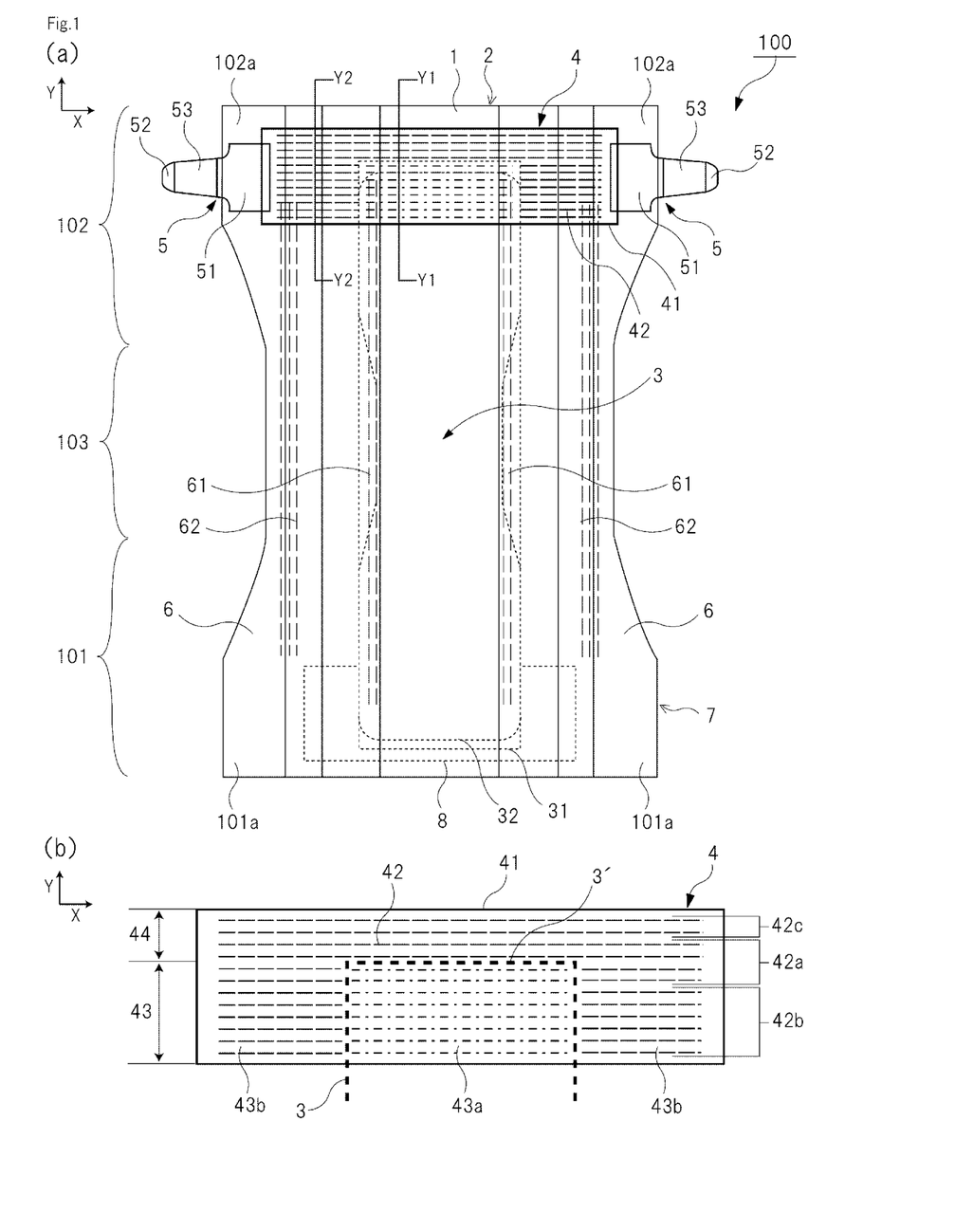
FIG. 1(a) illustrates a developed diagram of the disposable diaper.
FIG. 1(b) illustrates an extracted and enlarged stretchable sheet.
Figure 2:
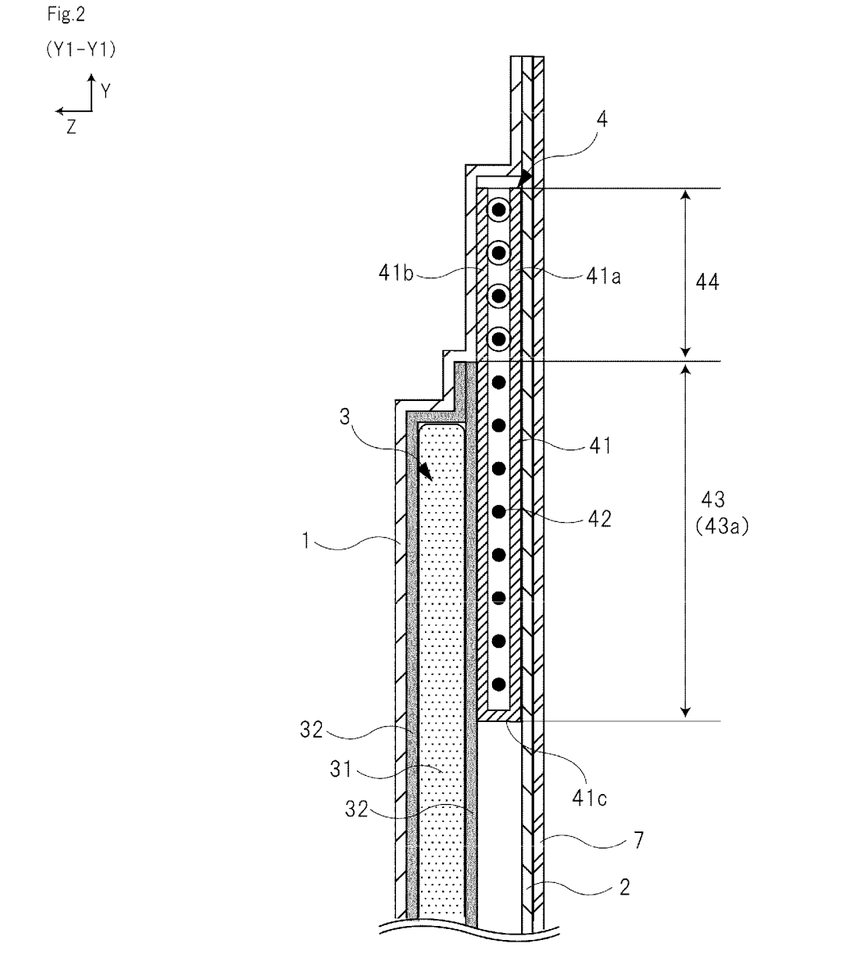
FIG. 2 illustrates an outline of a cross section of line Y1-Y1 illustrated in FIG. 1(a).
Figure 3:
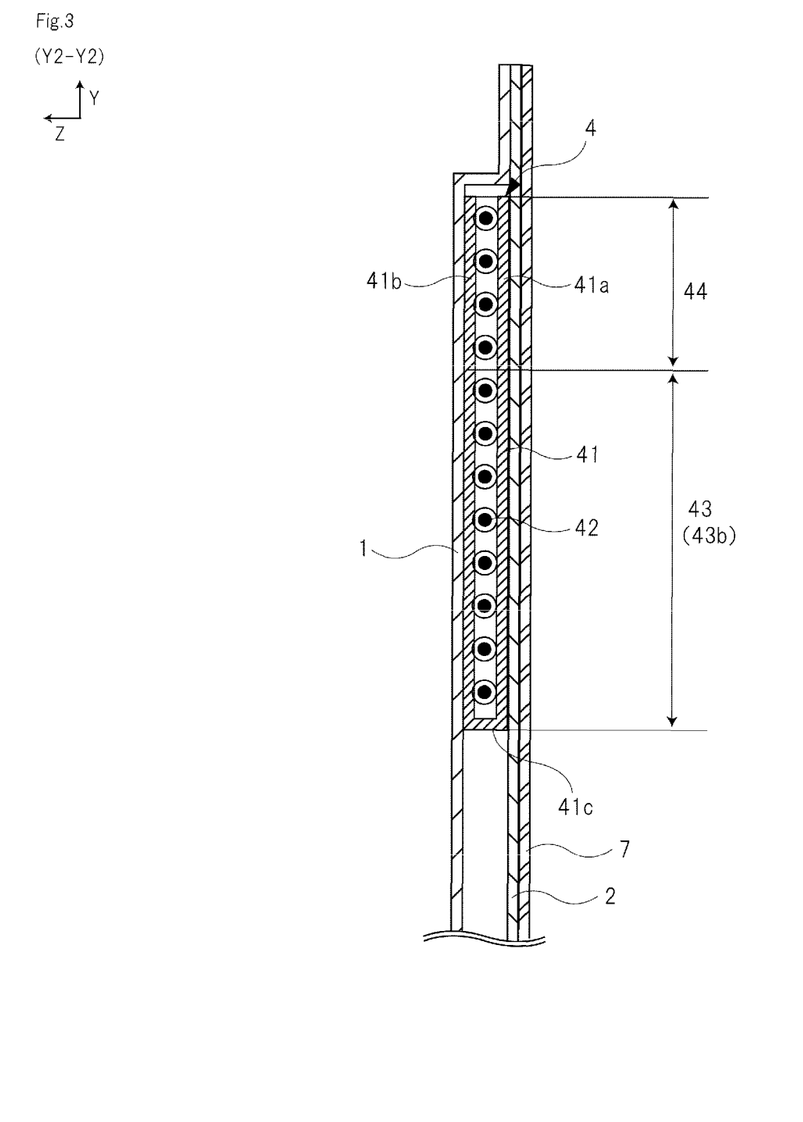
FIG. 3 illustrates an outline of a cross section of line Y2-Y2 illustrated in FIG. 1(a).

FIG. 2 illustrates an outline of a cross section of a disposable diaper cut in line Y1-Y1 illustrated in FIG. 1(a). Further, FIG. 3 illustrates an outline of a cross section of a state in which a disposable diaper is cut in line Y2-Y2 illustrated in FIG. 1(a). FIGS. 2 and 3 mainly illustrate the stretchable sheet 4 of a disposable diaper according to an embodiment. Note that, in FIGS. 2 and 3, sheet members that configure the disposable diaper are drawn to have conceptual thickness. However, originally, the various sheet materials are very thin, and have little thickness.

As illustrated in FIGS. 1(a) and 1(b) to 3, the stretchable sheet 4 is configured from a non-stretchable base material sheet 41, and a plurality of thread-like or belt-like stretchable elastic stretchable members 42. The plurality of elastic stretchable members 42 extends along the width direction of the diaper, and is arranged between the base material sheets 41 in an extended state at intervals in the length direction of the diaper. In the embodiment illustrated in FIG. 2, the base material sheet 41 is configured from one sheet member, and is folded at a folded part 41c positioned near the crotch part, and configures an inner surface part 41a positioned at the skin contact surface side and an outer surface part 41b positioned at the skin non-contact surface side. Then, the plurality of elastic stretchable members 42 is sandwiched between the inner surface part 41a and the outer surface part 41b of the base material sheet 41 in an extended state. Therefore, when the plurality of elastic stretchable members 42 contracts, the base material sheet 41 is subject to the effect of contractive force of the stretchable members 42 and is contract, so that gathers (pleats) having high cushioning properties are formed in the stretchable sheet 4.

The stretchable sheet 4 having the above-described basic configuration lies between the top sheet 1 and the back sheet 2. Especially, as illustrated in FIG. 2, in the present embodiment, one part of the stretchable sheet 4 close to an upper end (an upper part of FIG. 2) at the side of the back body part 102 is arranged between the top sheet 1 and the back sheet 2, and the other part (a lower part of FIG. 2) close to the crotch part is arranged between the absorber 3 and the back sheet 2. Therefore, in the present embodiment, the outer surface part 41b positioned at the skin non-contact surface side, of the base material sheet 41 of the stretchable sheet 4, is entirely in contact with the back sheet 2. Meanwhile, the inner surface part 41a positioned at the skin contact surface side, of the base material sheet 41 of the stretchable sheet 4, is divided into a surface (a surface positioned in an overlapping part 43) that is in contact with the absorber 3, and a surface (a surface positioned in a non-overlapping part 44) that is in contact with the top sheet.

As illustrated in FIG. 2, the inner surface part 41a of the base material sheet 41 of the stretchable sheet 4 has the surface being in contact with the top sheet 1 and the surface being in contact with the absorber 3, and the outer surface part 41b is in contact with the back sheet 2. In this case, it is favorable that the inner surface part 41a of the base material sheet 41 and the top sheet 1 are continuously joined in the length direction and the width direction. Further, it is favorable that the outer surface part 41b of the base material sheet 41 and the back sheet 2 are continuously joined in the length direction and the width direction. As described above, the base material sheet 41 is continuously joined with the top sheet 1 and the back sheet 2, so that fine gathers (pleats) are formed on the top sheet 1 and the back sheet 2 in association with the contraction of the elastic stretchable members 42 sandwiched by the base material sheets 41, and the appearance and the hand feeling of the diaper becomes better and positional deviation of the stretchable sheet 4 is prevented.

On the other hand, the base material sheet 41 and the absorber 3 (core wrap sheet 32) may be continuously joined in the length direction and the width direction, may be intermittently joined in the width direction, or may not be joined. Especially, in the present invention, it is favorable that the base material sheet 41 and the absorber 3 are not joined. The base material sheet 41 is not joined with the absorber 3, so that the contract force is less likely to be transmitted to the absorber 3 when the elastic stretchable members 42 sandwiched by the base material sheets 41 contract, and the shape of the absorber 3 is deformed and occurrence of unnecessary wrinkles or twists can be prevented.

Note that intermittent joining of the base material sheet 41 and the absorber 3 in the width direction means to alternately provide joined parts and non-joined parts along the width direction between the base material sheet 41 and the absorber 3.

Further, it is favorable that a vicinity of a length-direction end edge of the absorber 3 is joined with the base material sheet 41 even if the base material sheet 41 of the stretchable sheet 4 and the core wrap sheet 32 of the absorber 3 are not joined. For example, it is favorable that the absorber 3 is joined with the base material sheet 41 in a length direction range from a length-direction end edge 3' at the side overlapping with the stretchable sheet 4, to 1 to 30 mm, 5 to 25 mm, or 10 to 20 mm, and other parts are not joined with the base material sheet 41. As described above, only the vicinity of the length-direction end edge of the absorber 3 is joined with the stretchable sheet 4, whereby the end of the absorber 3 is fixed, and losing shape of the absorber 3 can be prevented.

As illustrated in FIGS. 1(a) and 1(b), in the present embodiment, the stretchable sheet 4 lying between the top sheet 1 and the back sheet 2 is divided into the overlapping part 43 close to the crotch part 103 and the non-overlapping part 44 close to an end edge of the back body part, in the length direction. The overlapping part 43 of the stretchable sheet 4 is a part including a region overlapping with a part of the absorber 3 as viewed in the width direction. That is, as illustrated in FIGS. 1(a) and 1(b), the overlapping part 43 is divided into a central region 43a overlapping with an end part of the absorber 3 at the back body part side, and side regions 43b positioned outside the central region 43a in the width direction. Therefore, the elastic stretchable members 42 arranged in the overlapping part 43 of the stretchable sheet 4 overlap with the absorber 3 in the central region 43a, and do not overlap with the absorber 3 in the side regions 43b. On the other hand, the non-overlapping part 44 of the stretchable sheet 4 does not overlap with the absorber 3 as viewed in the width direction. Therefore, the elastic stretchable members 42 arranged in the non-overlapping part 44 of the stretchable sheet 4 do not overlap with the absorber 3.

Note that the embodiment in which the stretchable sheet 4 is divided into the overlapping part 43 and the non-overlapping part 44 is a favorable embodiment in the present invention. The stretchable sheet 4 may just have at least the overlapping part 43, and does not necessarily have the non-overlapping part 44.

In FIGS. 1(*a*) and 1(*b*), a part joined between the base material sheets 41, of the plurality of elastic stretchable members 42 included in the stretchable sheet 4, is illustrated by "dotted lines", and a part not joined between the base material sheet 41 is illustrated by "alternate long and short dash lines". Further, in FIGS. 2 and 3, a part joined with the base material sheet 41, of the plurality of elastic stretchable members 42 included in the stretchable sheet 4, is illustrated by being circled with a "circle (○)". FIG. 2 is a cross sectional view in line Y1-Y1 illustrated in FIG. 1(*a*), and the boundary of the cross section of Y1-Y1 is positioned in the central region 43*a*. Further, FIG. 2 is a cross sectional view of line Y2-Y2 illustrated in FIG. 1(*a*), and the boundary of the cross section of Y2-Y2 is positioned in the side region 43*b*.

As illustrated in the drawings, the plurality of elastic stretchable members 42 is continuously arranged in the overlapping part 43 of the stretchable sheet 4. The "continuously" referred here means that the elastic stretchable members 42 extend from one side to the other side of the overlapping part 43 along the width direction, and the entire part is arranged to be stretchable, and means that the elastic stretchable members 42 is not in a non-stretchable state by being cut or bonded with pressure in the middle. The plurality of elastic stretchable members 42 continuously arranged in the overlapping part 43 of the stretchable sheet 4 is not joined between the base material sheets 41 in the central region 43*a* overlapping with the absorber 3, and on the other hand, the plurality of elastic stretchable members 42 is joined between the base material sheets 41 in the side regions 43*b* not overlapping with the absorber 3. In this way, while the elastic stretchable members 42 arranged in the overlapping part 43 continuously exist in the width direction without being cut (without being in the non-stretchable state), the portion positioned in the central region 43*a* is in a non-joined state with the base material sheet 41, and the part positioned in the side region 43*b* is in a joined state with the base material sheet 41.

On the other hand, the plurality of elastic stretchable members 42 is continuously arranged in the non-overlapping part 44 of the stretchable sheet 4. The plurality of elastic stretchable members 42 arranged in the non-overlapping part 44 of the stretchable sheet 4 continuously exist in the width direction without being cut, and are joined between the base material sheets 41.

As described above, in the present invention, basically, the elastic stretchable members 42 included in the stretchable sheet 4 is joined between the base material sheets 41 except the region (central region 43*a*) overlapping with the absorber 3 in the thickness direction. However, even in the region (central region 43*a*) where the stretchable sheet 4 and the absorber 3 overlap with each other, the elastic stretchable members 42 exist in the stretchable state without being joined between the base material sheets 41. With such a configuration, the elastic stretchable members 42 exist in the central region 43*a* where the stretchable sheet 4 and the absorber 3 overlap with each other, so that the absorber 3 is closely attached to the skin of the wearer when the elastic stretchable members 42 contract. On the other hand, the elastic stretchable members 42 are not joined between the base material sheets 41 in the central region 43*a* where the stretchable sheet 4 and the absorber 3 overlap with each other. Therefore, the contracting force of the elastic stretchable members 42 is less likely to be transmitted to the absorber 3 even if the elastic stretchable members 42 contract, and occurrence of wrinkles or twists in the absorber 3 can be prevented.

As a method to join the elastic stretchable members 42 with the base material sheet 41, a known method can be employed. The method to join the elastic stretchable members 42 can be selected from a joining method with a hot-melt adhesives and a joining method by thermocompression. It is favorable that the elastic stretchable members 42 are continuously joined with the base material sheet 41 in a place (the side regions 43*b* of the overlapping part 43 and the non-overlapping part 44) where the joining is necessary. For example, the hot-melt adhesive is applied to the necessary place of the elastic stretchable members 42, and the elastic stretchable members 42 to which the hot-melt adhesives is applied may be inserted between the base material sheets 41.

Further, as illustrated in FIGS. 1(*a*) and 1(*b*), it is favorable that the elastic stretchable members 42 included in the stretchable sheet 4 are arranged between the base material sheets 41 at approximately constant intervals in the length direction of the diaper. It is favorable that the intervals of adjacent elastic stretchable members 42 are approximately the same, and can be 0.3 to 10 mm, or 0.5 to 0.8 mm. However, it is substantially difficult to cause the intervals of the plurality of elastic stretchable members 42 to completely accord with each other. Therefore, it is acceptable if the intervals are deviated within a range of error of ±5% or less where an average value of the intervals of the plurality of elastic stretchable members 42 is 100%. As described above, the intervals of the elastic stretchable members 42 are approximately constant, whereby uniform gathers (pleats) are caused in the part around the waist of the diaper, the appearance becomes better, and the hand feeling and texture of the diaper becomes favorable.

Further, as illustrated in FIG. 1(*a*), the stretchable sheet 4 is arranged with an interval from the length-direction end edge of the back body part 102 side of the disposable diaper. It is favorable that the interval between an upper edge of the stretchable sheet 4 and an upper edge of the back body part 102 of the disposable diaper is 5 to 30 mm, or 10 to 20 mm, for example. As described above, the stretchable sheet 4 is arranged with the interval from the length-direction end edge of the diaper, whereby hardness of the stretchable sheet 4 itself is less likely to be transmitted to the wearer, and the feeling of wearing of the diaper is improved.

Further, as illustrated in FIG. 1(*b*), the elastic stretchable members 42 positioned in the vicinity of the length-direction end edge 3' of the absorber 3, of the plurality of elastic stretchable members 42 included in the stretchable sheet 4, are caused to be end edge vicinity stretchable members 42*a*. For example, one to six elastic stretchable members 42 close to the length-direction end edge 3' of the absorber 3, of the plurality of elastic stretchable members 42, may be caused to be the end edge vicinity stretchable members 42*a*. In the example illustrated in FIG. 1(*b*), the four elastic stretchable members 42 close to the length-direction end edge 3' of the absorber 3 are the end edge vicinity stretchable members 42*a*. In this case, it is favorable that contractive force (A) with which the end edge vicinity stretchable members 42*a*, of the plurality of elastic stretchable members 42 included in the stretchable sheet 4, contract the base material sheet 41 is set to be lower than the contractive force of other elastic stretchable members 42. That is, the vicinity of the length-direction end edge 3' of the absorber 3 is subject to the effect of the contractive force of the elastic stretchable members 42 and is especially more likely to be deformed. Therefore, to suppress the deformation of the absorber 3, it is favorable to set the contractive force (A) of the end edge vicinity stretchable members 42a to be low.

Further, as illustrated in FIG. 1(*b*), the elastic stretchable members 42 other than the end edge vicinity stretchable members 42a, of the plurality of elastic stretchable members 42 arranged in the overlapping part 43 of the stretchable sheet 4, are caused to be overlapping elastic stretchable members 42b. Further, the elastic stretchable members 42 other than the end edge vicinity stretchable members 42a, of the plurality of elastic stretchable members 42 arranged in the non-overlapping part 44 of the stretchable sheet 4, are caused to be non-overlapping elastic stretchable members 42c. In this case, it is favorable that the contractive force (A) of the end edge vicinity stretchable members 42a, contractive force (B) of the overlapping elastic stretchable members 42b, and contractive force (C) of the non-overlapping elastic stretchable members 42c satisfy relationship of (C)>(B)>(A). With such relationship, appropriate stretchability can be provided to the part around the waist of the diaper while the amount of deformation of the absorber 3 being subject to the effect of the contractive force of the plurality of elastic stretchable members 42 is suppressed to be small.

Further, it is possible to adjust that the contractive force (A) of the end edge vicinity stretchable members 42a, the contractive force (B) of the overlapping elastic stretchable members 42b, and the contractive force (C) of the non-overlapping elastic stretchable members 42c satisfy relationship of (B)>(C)>(A), in place of the above-described relationship. In this case, high stretchability can be provided to both side parts (side regions 43b) of the absorber 3, while the deformation in the vicinity of the length-direction end edge 3' of the absorber 3 is suppressed to be small.

As the adjustment of the "contractive force", an extension rate of when the elastic stretchable members are joined with the base material sheet 41 may be just be adjusted, for example, when a plurality of elastic stretchable members having the same diameter is used. The "extension rate" referred here is a rate of an increased amount of the length elastic stretchable member in the extended state where the length of the elastic stretchable member in a contract state (natural state) is 100%. For example, when one with the length of 10 cm is extended to 20 cm, the extension rate thereof is 200%. The contractive force of the elastic stretchable members becomes higher as the extension rate of the elastic stretchable members when being joined with the base material sheet is higher. Further, it is also possible to adjust the contractive force of the elastic stretchable members by adjusting the diameters of the elastic stretchable members. By its nature, the contractive force of the elastic stretchable members becomes larger as the diameters are larger where the extension rates are the same.

Note that the "contractive force" is stress applied to the base material sheet when the elastic stretchable members are joined with the base material sheet in a state of being extended in the width direction of the diaper. The contractive force of the elastic stretchable members may just be measured as follows. That is, first, a region to be measured is cut from an extended sheet and a sample piece is obtained. One end part of the sample piece in the width direction is inserted into one chuck of a tensile test device and the other end part is inserted into the other chuck, and a tensile test is performed along the width direction. Then, the stress applied to the chucks of when the test piece is pulled such that the distance between the chucks becomes $(\alpha+\beta)/2$ is measured, where a distance between the chucks (a length at the time of natural contraction) in a state where the sample piece is naturally contracted without being pulled is $\alpha$, and a distance between the chucks (a length at the time of maximum extension) of when the sample piece is pulled to a state where no contraction by the elastic stretchable members is caused is $\beta$. Then, a measured value is divided by the length of a front-back direction of the sample piece, and a divided value is obtained as the contractive force. In this way, the magnitude of the stretching force of the elastic stretchable members can be compared.

As illustrated in FIG. 1(*a*), the pair of fastening parts 5 is respectively attached to the right and left side flaps 102a formed in the back body part 102 of the disposable diaper 100. Further, the stretchable sheet 4 is arranged in the back body part 102 of the disposable diaper 100, similarly to the pair of fastening parts 5. At this time, it is favorable that the plurality of elastic stretchable members 42 included in the stretchable sheet 4 is positioned in an inner region of the fixed ends 51 in the width direction without overlapping with the fixed ends 51 of the pair of fastening parts 5. As described above, the elastic stretchable members 42 of the stretchable sheet 4 are provided in the inner region of the fixed ends 51 of the pair of fastening parts 5 in the width direction, whereby the part around the waist of the diaper becomes extended when the fastening parts 5 are pulled when the disposable diaper is applied, and application work of the tape-type disposable diaper becomes easy.

Further, as illustrated in FIG. 1(*a*), it is favorable that the both side end parts of the base material sheet 41 that configure the stretchable sheet 4 in the width direction overlap with the fixed ends 51 of the pair of fastening parts 5 in the thickness direction. That is, as illustrated in FIG. 1(*a*), while the elastic stretchable members 42 of the stretchable sheet 4 do not overlap with the fixed ends 51 of the fastening parts 5, the both end parts of the base material sheet 41 in the width direction overlap with the fixed ends 51 of the fastening parts 5. With such a configuration, tensile force can be easily transmitted to the base material sheet 41 of the stretchable sheet 4 when the pair of fastening parts 5 is outwardly pulled in the width direction. Then, the tensile force to the outside in the width direction is appropriately transmitted to the base material sheet 41 of the stretchable sheet 4, so that the elastic stretchable members 42 sandwiched between the base material sheets 41 can be easily outwardly extended in the width direction. Therefore, the application work of the tape-type disposable diaper becomes easier.

Figure 4:
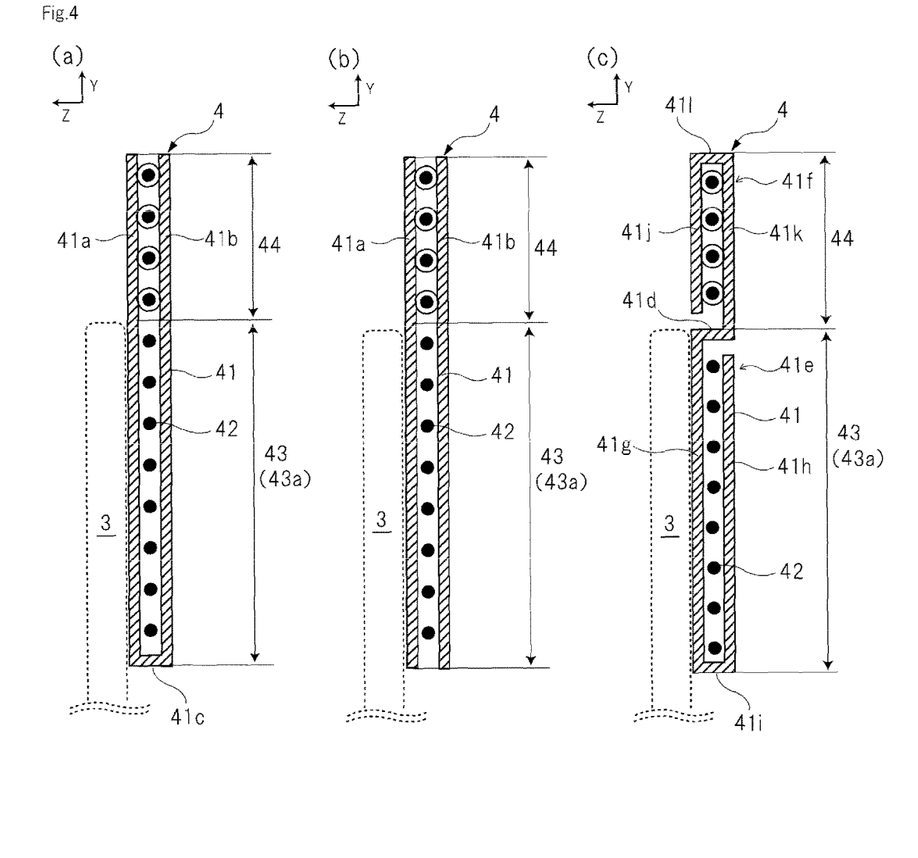
FIG. 4(a) illustrates an example in which a base material sheet is formed such that one sheet member is folded in half.
FIG. 4(b) illustrates an example in which a base material sheet is formed of two sheet members.
FIG. 4(c) illustrates an example in which a base material sheet is configured from one sheet member, and the cross section of the base material sheet is formed in a figure-eight manner.

Following that, embodiments to sandwich a plurality of elastic stretchable members 42 between base material sheets 41 will be described with reference to FIGS. 4(*a*) to 4(*c*), and 5(*a*) and 5(*b*). FIGS. 4(*a*) to 4(*c*), and 5(*a*) and 5(*b*) illustrate examples of variations applicable to the present invention. Note that the embodiments to sandwich the plurality of elastic stretchable members 42 between the base material sheets 41 are not limited to the examples described below. Note that, similarly to the cross section of FIG. 2, FIGS. 4(*a*) to 4(*c*), and 5(*a*) and 5(*b*) illustrate cross sectional shapes of a state where a stretchable sheet 4 is cut in a length direction in a central region 43a of the stretchable sheet 4. Further, in FIGS. 4(*a*) to 4(*c*), and 5(*a*) and 5(*b*), the absorber 3 is illustrated by the "dotted line" for clarification of arrangement relationship between the stretchable sheet 4 and the absorber 3.

The stretchable sheet 4 illustrated in FIG. 4(*a*) has a similar configuration to the stretchable sheet 4 illustrated in FIG. 2. That is, in the example illustrated in FIG. 4(*a*), the base material sheet 41 of the stretchable sheet 4 is configured from one sheet member. The base material sheet 41 is folded at a folded part 41*c* provided at a position of a crotch part side (a lower side of FIG. 4(*a*)), and is divided into an inner surface part 41*a* positioned at a skin contact surface side and an outer surface part 41*b* positioned at a skin non-contact surface side, having the folded part 41*c* as a boundary. An upper end edge side (an upper side of FIG. 4) of the base material sheet 41 is open, and the sheet member does not have an overlapping part in a two-ply manner. The embodiment to fold the base material sheet 41 in half and to sandwich the elastic stretchable members 42 as illustrated in FIG. 4(*a*) is typically called U-wrap structure.

In the example illustrated in FIG. 4(*a*), the base material sheet 41 and the absorber 3 may be continuously joined in a length direction and a width direction, may be intermittently joined in the width direction, or may not be joined. Especially, in the present invention, it is favorable to join the base material sheet 41 and the absorber 3. The base material sheet 41 is not joined with the absorber 3, so that contractive force is less likely to be transmitted to the absorber 3 when the elastic stretchable members 42 sandwiched by the base material sheets 41 contract, and the shape of the absorber 3 is deformed and occurrence of unnecessary wrinkles or twists can be prevented. Further, it is favorable that a vicinity of a length-direction end edge of the absorber 3 is joined with the base material sheet 41 even if the base material sheet 41 of the stretchable sheet 4 and a core wrap sheet 32 of the absorber 3 are not joined. For example, it is favorable that the absorber 3 is joined with the base material sheet 41 in a length direction range from a length-direction end edge 3' at the side overlapping with the stretchable sheet 4, to 1 to 30 mm, 5 to 25 mm, or 10 to 20 mm, and other parts are not joined with the base material sheet 41.

FIG. 4(*b*) illustrates an example in which the base material sheet 41 is configured from two sheet members. As illustrated in FIG. 4(*b*), an inner surface part 41*a* and an outer surface part 41*b* of the base material sheet 41 can be configured from separate sheet members. In this way, a plurality of elastic stretchable members 42 may be sandwiched by the sheet member that configures the inner surface part 41*a* and the sheet member that configures the outer surface part 41*b*. In the example illustrated in FIG. 4(*b*), the base material sheet 41 and the absorber 3 may be continuously joined in a length direction and a width direction, may be intermittently joined in the width direction, or may not be joined. Especially, it is favorable that a vicinity of a length-direction end edge 3' of the absorber 3 at the side overlapping with a stretchable sheet 4 is joined with the base material sheet 41, and other parts are not joined with the base material sheet 41.

FIG. 4(*c*) illustrates an example in which the base material sheet 41 is configured from one sheet member, and an intersection part 41*d* that traverses elastic stretchable members 42 in a thickness direction (a right and left direction of FIG. 4(*c*)). To be specific, in the example illustrated in FIG. 4(*c*), the base material sheet 41 is divided into a lower part 41*e* (a lower side of FIG. 4(*c*)) close to a crotch part in the length direction, and an upper part 41*f* (an upper side of FIG. 4(*c*)) close to a part in the length direction, having the intersection part 41*d* as a boundary. In the lower part 41*e* of the base material sheet 41, a lower part inner surface 41*g* positioned at a skin contact surface side and a lower part outer surface 41*h* positioned at a skin non-contact surface side are integrally coupled through a lower edge folded part 41*i* corresponding to a lower edge of the stretchable sheet 4. A plurality of elastic stretchable members 42 is arranged between the lower part inner surface 41*g* and the lower part outer surface 41*h*. Further, in the upper part 41*f* of the base material sheet 41, an upper part inner surface 41*j* positioned at the skin contact surface side and an upper part outer surface 41*k* positioned at the skin non-contact surface side are integrally coupled through an upper edge folded part 41*l* corresponding to an upper edge of the stretchable sheet 4. The plurality of elastic stretchable members 42 is arranged between the upper part inner surface 41*j* and the upper part outer surface 41*k*. Then, in the example illustrated in FIG. 4(*c*), the lower part inner surface 41*g* and the upper part outer surface 41*k* of the stretchable sheet 4 are integrally coupled through the intersection part 41*d* that traverses the elastic stretchable members 42 in the thickness direction. Note that, as another example, the lower part outer surface 41*h* and the upper part inner surface 41*j* of the stretchable sheet 4 may be integrally coupled through the intersection part 41*d*. As described above, in the example illustrated in FIG. 4(*c*), the cross section of the base material sheet 41 is approximately formed in a figure-eight manner. Especially, as illustrated in FIG. 4(*c*), it is favorable that the intersection part 41*d* is formed at a position traversing the stretchable sheet 4 in the thickness direction between the elastic stretchable members 42 arranged in an overlapping part 43 that overlaps with the absorber 3, and the elastic stretchable members 42 arranged in a non-overlapping part 44 not overlapping with the absorber 3. With such a configuration, the elastic stretchable members 42 are joined between the sheets in the upper part 41*f* of the base material sheet 41, and the elastic stretchable members 42 are not joined between the sheets in the lower part 41*e* of the base material sheet 41. As described above, the intersection part 41*d* is formed to partition the elastic stretchable members 42 joined between the sheets and the elastic stretchable members 42 not joined between the sheets, whereby contractive force of the elastic stretchable members 42 positioned in the upper part 41*f* of the base material sheet 41 is less likely to the transmitted to the absorber 3 that is in contact with the lower part 41*e* of the base material sheet 41. Therefore, the amount of deformation of the absorber 3 can be suppressed. In the example illustrated in FIG. 4(*c*), the base material sheet 41 and the absorber 3 may be continuously joined in the length direction and the width direction, may be intermittently joined in the width direction, or may not be joined. Especially, it is favorable that a vicinity of a length-direction end edge 3' of the absorber 3 at the side overlapping with the stretchable sheet 4 is joined with the base material sheet 41, and other parts are not joined with the base material sheet 41.

Figure 5:
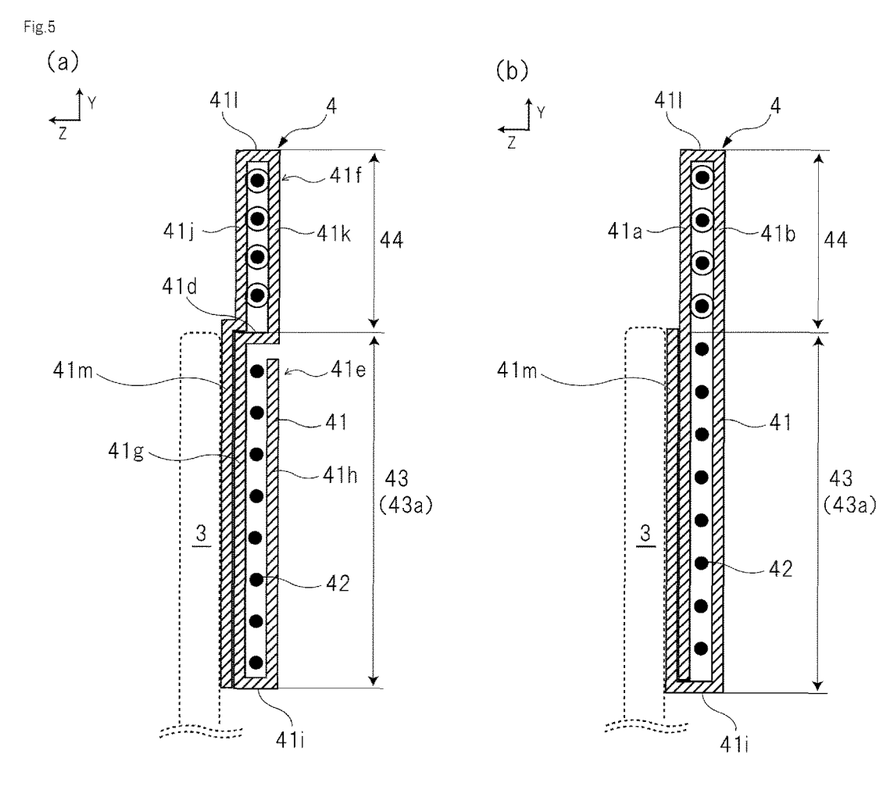
FIG. 5(a) illustrates an example in which the cross section of one base material sheet is formed in a figure-eight manner, and the base material sheets are layered in a two-ply manner between elastic stretchable members and an absorber.
FIG. 5(b) illustrates an example in which elastic stretchable members are wrapped by one base material sheet, and the base material sheets are layered in a two-ply manner between the elastic stretchable members and an absorber.

FIGS. 5(*a*) and 5(*b*) illustrate modifications of the embodiments illustrated in FIGS. 4(*a*) to 4(*c*).

FIG. 5(*a*) illustrates an application example of the structure of the stretchable sheet 4 described with reference to FIG. 4(*c*). In the example illustrated in FIG. 5(*a*), an upper part inner surface 41*j* of a base material sheet 41 has an extended part 41*m* extending toward a direction of a crotch part (a lower part of FIG. 5(*a*)). Then, the extended part 41*m* of the upper part inner surface 41*j* overlaps with a lower part inner surface 41*g* of the base material sheet 41. Therefore, two-ply or more base material sheets 41 are layered between elastic stretchable members 42 and an absorber 3 in an overlapping part 43 that overlaps with the absorber 3. That is, the extended part 41m of the upper part inner surface 41j and the lower part inner surface 41g of the base material sheet 41 are positioned between the elastic stretchable members 42 and the absorber 3 arranged in the overlapping part 43. With such a configuration, contractive force of the elastic stretchable members 42 can be less likely to be transmitted to the absorber 3 if the extended part 41m and the lower part inner surface 41g are not joined even if the extended part 41m of the upper part inner surface 41j of the base material sheet 41 and the absorber 3 are joined. That is, the lower part inner surface 41g that is directly in contact with the elastic stretchable members 42 is more likely to be contracted by the contractive force of the elastic stretchable member 42. However, the contractive force of the elastic stretchable members 42 is less likely to be transmitted to the extended part 41m layered on the lower part inner surface 41g without being joined therewith. Therefore, it can be said that the absorber 3 further layered on the extended part 41m is less likely to subject to an effect of the contractive force of the elastic stretchable members 42. As described above, two or more base material sheets 41 are layered between the elastic stretchable members 42 and the absorber 3 arranged in the overlapping part 43, whereby occurrence of wrinkles and twists in the absorber 3 can be prevented.

Note that, in the example illustrated in FIG. 5(a), the extended part 41m of the base material sheet 41 and the absorber 3 may be continuously joined in a length direction and a width direction, may be intermittently joined in the width direction, or may not be joined. Further, the extended part 41m of the base material sheet 41 and the lower part inner surface 41g may be continuously joined in the length direction and the width direction, may be intermittently joined in the width direction, or may not be joined.

For example, it is favorable that the extended part 41m of the base material sheet 41 and the absorber 3 are continuously joined, and the extended part 41m and the lower part inner surface 41g are not joined. The extended part 41m of the base material sheet 41 and the absorber 3 are joined, whereby losing shape and positional deviation of the absorber 3 can be prevented. Further, the extended part 41m and the lower part inner surface 41g are not joined, whereby the contractive force is less likely to be transmitted to the absorber 3 when the elastic stretchable members 42 sandwiched between the base material sheets 41 contract, and the shape of the absorber 3 is deformed and occurrence of unnecessary wrinkles and twists can be prevented.

Further, for example, the extended part 41m of the base material sheet 41 and the absorber 3 may not be joined, and the extended part 41m and the lower part inner surface 41g may be joined. Note that it is favorable that a vicinity of a length-direction end edge of the absorber 3 is joined with the extended part 41m in order to prevent the loosing shape of the absorber 3 even if the extended part 41m of the base material sheet 41 of the stretchable sheet 4 and the absorber 3 are not joined. For example, it is favorable that the absorber 3 is joined with the extended part 41m of the base material sheet 41 in a length direction range from the length-direction end edge at the side overlapping with the stretchable sheet 4, to 1 to 30 mm, 5 to 25 mm, or 10 to 20 mm, and other parts are not joined with the extended part 41m of the base material sheet 41.

Further, for example, the extended part 41m of the base material sheet 41 and the absorber 3 may not be joined, and the extended part 41m and the lower part inner surface 41g may also not be joined. Note that, similarly to the above, it is favorable that the vicinity of the length-direction end edge of the absorber 3 is joined with the extended part 41m even if the extended part 41m of the base material sheet 41 of the stretchable sheet 4 and the absorber 3 are not joined.

FIG. 5(b) illustrates another example of a structure of a stretchable sheet 4. In the example illustrated in FIG. 5(b), a base material sheet 41 is configured from one sheet member, and an inner surface part 41a and an outer surface part 41b are integrally coupled through an upper edge folded part 41l corresponding to an upper edge of a stretchable sheet 4. A plurality of elastic stretchable members 42 is sandwiched between the inner surface part 41 and the outer surface part 41b. Further, the outer surface part 41b has an extended part 41m extending in a direction (a lower part of FIG. 5(b)) where a crotch part exists. The extended part 41m of the outer surface part 41b is folded to a skin contact surface side at a lower edge folded part 41i corresponding to a lower edge of the stretchable sheet 4, and is layered on the inner surface part 41a. Accordingly, two-ply or more base material sheets 41 are layered between the elastic stretchable members 42 and the absorber 3 in an overlapping part 43 that overlaps with the absorber 3. That is, the inner surface part 41a and the extended part 41m of the outer surface part 42b of the base material sheet 41 are positioned between the elastic stretchable members 42 and the absorber 3 arranged in the overlapping part 43. With such a configuration, contractive force of the elastic stretchable members 42 is less likely to be transmitted to the absorber 3 if the extended part 41m and the inner surface part 41a are not joined even if the extended part 41m of the outer surface part 41b of the base material sheet 41 and the absorber 3 are joined. This point is similar to the above-described example of FIG. 5(a).

In the example illustrated in FIG. 5(b), similarly to the example of FIG. 5(a), the extended part 41m of the base material sheet 41 and the absorber 3 may be continuously joined in a length direction and a width direction, may be intermittently joined in the width direction, or may not be joined. Further, the extended part 41m and the lower part inner surface 41g of the base material sheet 41 may be continuously joined in the length direction and the width direction, may be intermittently joined in the width direction, and may not be joined.

For example, it is favorable that the extended part 41m of the base material sheet 41 and the absorber 3 are continuously joined, and the extended part 41m and the lower part inner surface 41g are not joined. Further, for example, the extended part 41m of the base material sheet 41 and the absorber 3 may not be joined, and the extended part 41m and the lower part inner surface 41g may be joined. Note that it is favorable that a vicinity of a length-direction end edge of the absorber 3 is joined with the extended part 41m in order to prevent loosing shape of the absorber 3 even if the extended part 41m of the base material sheet 41 of the stretchable sheet 4 and the absorber 3 are not joined. Further, for example, the extended part 41m of the base material sheet 41 and the absorber 3 may not be joined, and the extended part 41m and the lower part inner surface 41g may also not be joined.

Next, other modifications of structures of a stretchable sheet 4 will be described with reference to FIGS. 6(a) to 6(d).

Figure 6:
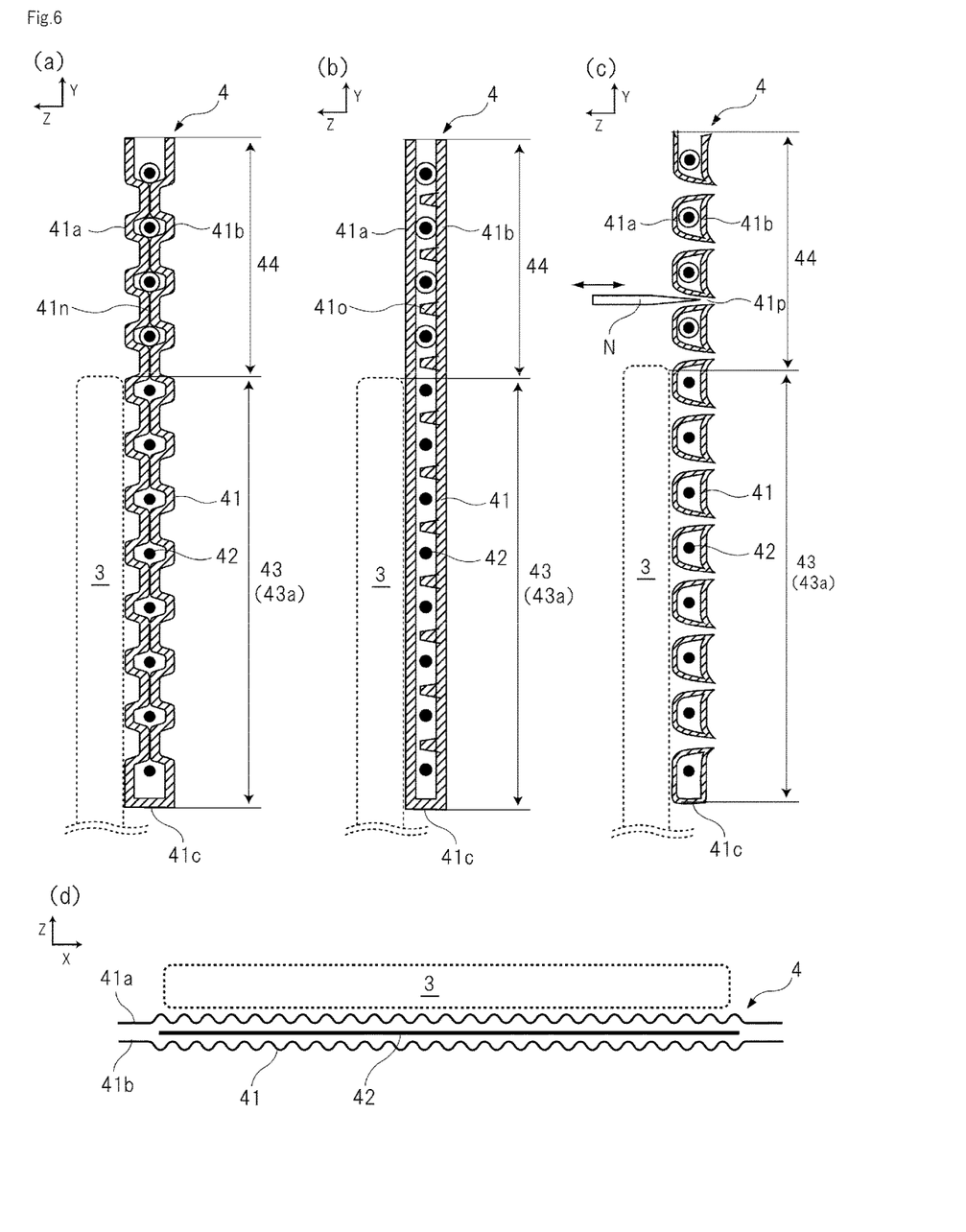
FIG. 6(a) illustrates an example in which an inner surface part and an outer surface part of a stretchable sheet folded in half are mutually joined in regions of gaps of elastic stretchable members.
FIG. 6(b) illustrates an example in which an outer surface part of a stretchable sheet folded in half has protrusions in regions of gaps of elastic stretchable members.
FIG. 6(c) illustrates an example in which an inner surface part and an outer surface part of a base material sheet are thermally welded in regions of gaps of elastic stretchable members with a heated needle.
FIG. 6(d) illustrates an example in which elastic stretchable members are fixed in a state where wrinkles are formed in an inner surface part and an outer surface part of a stretchable sheet.

In the example illustrated in FIG. 6(a), a base material sheet 41 that configures a stretchable sheet 4 is folded in half at a folded part 41c, and has an inner surface part 41a positioned at a skin contact surface side and an outer surface part 41b positioned at a skin non-contact surface side. A plurality of elastic stretchable members 42 is arranged between the inner surface part 41a and the outer surface part 41b of the base material sheet 41 at constant intervals in a length direction (an up and down direction of FIG. 6(a). Then, the inner surface part 41a and the outer surface part 41b of the base material sheet 41 are joined with each other in regions of gaps of adjacent elastic stretchable members 42. That is, a joined part 41n of the inner surface part 41a and the outer surface part 41b is formed in the regions of the gaps of the adjacent elastic stretchable members 42. As described above, the inner surface part 41a and the outer surface part 41b of the base material sheet 41 are joined in the regions between the elastic stretchable members 42 arranged at intervals, whereby deviation of the elastic stretchable members 42 in the length direction of the diaper can be prevented. Especially, in the present invention, the elastic stretchable members 42 arranged in an overlapping part 43 that overlaps with the absorber 3 are not joined with the base material sheet 41. Therefore, it is favorable to control the deviation of the elastic stretchable members in some way. Therefore, in the example of FIG. 6(a), the joined part n where the inner surface part 41a and the outer surface part 41b of the base material sheet 41 are joined is formed in the regions of the gaps of the adjacent elastic stretchable members 42, whereby the deviation of the elastic members is prevented. The inner surface part 41a and the outer surface part 41b may be joined, for example, using a hot-melt adhesives, or may be joined by heat sealing or ultrasonic sealing.

In the example illustrated in FIG. 6(b), a base material sheet 41 that configures a stretchable sheet 4 is folded in half at a folded part 41c, and has an inner surface part 41a positioned at a skin contact surface side and an outer surface part 41b positioned at a skin non-contact surface side. A plurality of elastic stretchable members 42 is arranged between the inner surface part 41a and the outer surface part 41b of a base material sheet 41 at constant intervals in a length direction (an up and down direction of FIG. 6(a)). Then, a sheet member that configures the outer surface part 41b (or the inner surface part 41a) is deformed, and a plurality of protrusions 410 protruding to a side facing the elastic stretchable members 42 is formed in regions of gaps of adjacent elastic stretchable members 42. For example, the protrusions 410 can be formed such that the base material sheet 41 is deformed to be locally bent so that the base material sheet 41 is protruded toward the side facing the elastic stretchable members 42. As described above, the protrusions 410 are formed in the regions of the gaps of the adjacent elastic stretchable members 42, whereby positional deviation of the elastic stretchable members 42 can be prevented.

In the example illustrated in FIG. 6(c), a base material sheet 41 that configures a stretchable sheet 4 is folded in half at a folded part 41c, and has an inner surface part 41a positioned at a skin contact surface side and an outer surface part 41b positioned at a skin non-contact surface side. A plurality of elastic stretchable members 42 is arranged between the inner surface part 41a and the outer surface part 41b of the base material sheet 41 at constant intervals in a length direction (an up and down direction of FIG. 6(c)). Then, a heated needle (heated needle N) penetrates regions of gaps of adjacent elastic stretchable members 42 from the inner surface part 41a to the outer surface part 41b, and a plurality of perforations 41p is provided, so that the inner surface part 41a and the outer surface part 41b are thermobonded. The size of the perforation 41p is favorably a diameter of 0.2 to 0.5 mm when only the thermobonding of the inner surface part 41a and the outer surface part 41b are intended. Further, the size of the perforation 41p is favorably a diameter of 0.5 to 10 mm when providing of breathability by the perforations 41p to the stretchable sheet 4 is intended. By providing of relatively large perforations 41p in the stretchable sheet 4, the breathability and moisture permeability in a thickness direction of the stretchable sheet 4 are improved. To adjust the size of the perforation 41p, the heated needle N having a cross section diameter suitable for the purpose may just be selected and the perforations 41p may just be formed. As described above, the inner surface part 41a and the outer surface part 41b are thermobonded while the perforations 41p are provided by the heated needle N, in the regions of the gaps of the adjacent elastic stretchable members 42, whereby the positional deviation of the elastic stretchable members 42 can be prevented.

FIG. 6(d) is a cross sectional view illustrating a state in which a stretchable sheet 4 is cut along a width direction of a disposable diaper in which elastic stretchable members 42 extend, which is different from FIGS. 6(a) to 6(c). In the example illustrated in FIG. 6(d), a base material sheet 41 that configures the stretchable sheet 4 is folded in half, and has an inner surface part 41a positioned at a skin contact surface side and an outer surface part 41b positioned at a skin non-contact surface side. A plurality of elastic stretchable members 42 is arranged between the inner surface part 41a and the outer surface part 41b. Here, in the example illustrated in FIG. 6(d), deformation of fine wrinkle shapes is provided to the base material sheet 41 so that unevenness is formed in a thickness direction of a sheet member, before the elastic stretchable members 42 in an extended state are sandwiched between the inner surface part 41a and the outer surface part 41b of the base material sheet 41. Then, the elastic stretchable members 42 in the extended state are sandwiched and fixed between the inner surface part 41a and the outer surface part 41b in a state where the wrinkles are remained in the base material sheet 41. In this way, the stretchable sheet 4 with the structure illustrated in FIG. 6(d) is formed. As described in the example, in the normal stretchable sheet 4, gathers are formed and cushioning properties are exerted in the thickness direction in a state where the elastic stretchable members 42 contract. However, in the normal stretchable sheet 4, the gathers are not formed and the cushioning properties in the thickness direction cannot be expected in a state where the elastic stretchable members 42 are completely extended. Therefore, in the example illustrated in FIG. 6(d), the deformation of fine wrinkle shapes is provided to the base material sheet 41 before the elastic stretchable members 42 are sandwiched between the inner surface part 41a and the outer surface part 41b so that the cushioning properties are exerted in the base material sheet 41 even in the state where the elastic stretchable members 42 are completely extended. Accordingly, the wrinkles with unevenness in the thickness direction are remained in the base material sheet 41 even in the state where the elastic stretchable members 42 are completely extended. Therefore, the stretchable sheet 4 can have appropriate cushioning properties on a steady basis.

As a material of the base material sheet 41 that configures the stretchable sheet 4, a known material can be appropriately used. For example, the base material sheet 41 is favorably hydrophobic. Examples of the material that configures the base material sheet 41 include nonwoven fabric and a film. Further, as a raw material that forms the base material sheet 41, polyethylene, polypropylene, polyester, or the like can be used. However, the raw material is not limited to the examples. When the base material sheet 41 is configured from nonwoven fabric, the nonwoven fabric can be obtained such that the raw material such as polyethylene is made into fiber, and the fiber is accumulated and bound.

Examples of a method to obtain the nonwoven fabric include a spunbonding method, a spunbonding/meltblowing/spunbonding method (SMS method), an air-through method, and a point-bonding method. When the base material sheet 41 is configured from a film, use of a polyethylene film is most favorable. In addition, as the base material sheet 41, one in which the nonwoven fabric and the film are layered may be used.

Further, as a material of the elastic stretchable members 42 that configure the stretchable sheet 4, a known material can be appropriately used. For example, for the elastic stretchable members 42, thread-like elastic rubber or flat elastic rubber can be applied. As such a rubber material, a material such as styrene-based rubber, olefin-based rubber, urethane-based rubber, ester-based rubber, polyurethane, polyethylene, polystyrene, styrene-butadiene, silicone, or polyester can be used. Further, for the stretchable members, thermoplastic elastomer, a plastic sheet, or a known member having stretchability such as a rubber sheet can be used, for example. Further, the number of elastic stretchable members 42 arranged between the base material sheets 41 can be appropriately adjusted according to use. For example, the elastic stretchable members 42 may be 4 to 20, 8 to 16, 10 to 14, or 12.

In the specification of the present application, favorable embodiments of the present invention have been mainly described with reference to the drawings in order to express details of the present invention. However, the present invention is not limited to the embodiments, and includes changed forms and modified forms that are apparent for a person skilled in the art, based on the matters described in the specification of the present application.

For example, in the specification of the present application, description has been given using an example where the disposable diaper is a tape-type diaper. However, the disposable diaper is not limited to the tape-type diaper, and the present invention can be applied to a pant-type present invention. The pant-type disposable diaper is a diaper having a front body part, a back body part, and a crotch part positioned between the front and back body parts, and in which both side parts of the front body part in a width direction and both side parts of the back body part in the width direction are corresponded and joined in advance, so that an opening around the waist and leg-surrounding openings are formed. The pant-type disposable diaper is applied to the wearer such that both legs of the wearer are inserted into the opening around the waist, and the legs are put out through the right and left leg-surrounding openings. As described above, when the disposable diaper of the present invention is a pant-type diaper, the stretchable sheet unique to the present invention may just be arranged in both parts or one part around the waist of the front and back body parts.

INDUSTRIAL APPLICABILITY

The present invention relates to a disposable diaper for elder persons and infants, for example. Therefore, the disposable diaper of the present invention can be favorable used in the industries related to nursing care and child care, and the like.

REFERENCE SIGNS LIST

1 Top sheet
2 Back sheet
3 Absorber
4 Stretchable sheet
5 Fastening part
6 Side sheet
7 Cover sheet
8 Front patch
41 Base material sheet
42 Elastic stretchable member
42 Overlapping part
43a Central region
43b Side region
44 Non-overlapping part
51 Fixed end
52 Protruding part
53 Engaging member
61 Three-dimensional gather stretchable member
62 Leg-surrounding gather stretchable member
100 Disposable diaper

The invention claimed is:

1. A tape-type disposable diaper comprising:
a liquid permeable top sheet;
a liquid impermeable back sheet;
an absorber lying between the top sheet and the back sheet and covering a crotch part; and
a stretchable sheet lying between the top sheet and the back sheet and overlapping with a part of the absorber, in a front body part or a back body part, and
a fastening part attached to both of right and left side parts of one of the front body part and the back body part so as to protrude from both of right and left side edges toward outsides in a width direction of the disposable diaper,
wherein the fastening part is attachable to an outer surface of the other one of the front body part and the back body part,
wherein the stretchable sheet includes
a base material sheet configured from one sheet member which is folded at least one point to configure an inner surface part positioned at a skin contact surface side and an outer surface part positioned at a skin non-contact surface side,
a plurality of elastic stretchable members extending along the width direction, and arranged in an extended state at intervals in a length direction of the disposable diaper, between the inner surface part and the outer surface part of the base material sheets, and
an overlapping part overlapping with the part of the absorber in the width direction,
wherein the plurality of elastic stretchable members is continuously arranged along the width direction in the overlapping part,
wherein the plurality of elastic stretchable members is not joined between the inner surface part and the outer surface part of the base material sheet in a central region of the overlapping part, wherein the central region is overlapping with the part of the absorber,
wherein the plurality of elastic stretchable members is joined between the inner surface part and the outer surface part of the base material sheet in side regions positioned outside the central region in the width direction,
wherein the stretchable sheet is arranged in the front body part or the back body part together with the fastening part, and
wherein the plurality of elastic stretchable members is positioned at inner sides in the width direction of right and left side fixed ends where the fastening part is fixed to.

2. The disposable diaper according to claim 1, wherein
the stretchable sheet further includes a non-overlapping part not overlapping with the absorber as viewed in the width direction, and
the plurality of elastic stretchable members is continuously arranged along the width direction and joined between the inner surface part and the outer surface part of the base material sheets, in the non-overlapping part.

3. The disposable diaper according to claim 1 or 2, wherein
the plurality of elastic stretchable members included in the stretchable sheet is arranged at approximately constant intervals in the length direction.

4. The disposable diaper according to claim 1 or 2, wherein
the stretchable sheet is arranged with an interval from an end edge of the front body part or the back body part in the length direction.

* * * * *